United States Patent
Fagon et al.

(10) Patent No.: US 8,802,059 B2
(45) Date of Patent: Aug. 12, 2014

(54) ALGAL EXTRACT-BASED COMPOSITION FOR ORO-DENTAL USE

(75) Inventors: Roxane Fagon, Saint Yvi (FR); Mélody Dutot, Paris (FR); Marc Hemon, Plouer sur Rance (FR)

(73) Assignee: YS Lab, Quimper (FR)

( * ) Notice: Subject to any disclaimer, the term of this patent is extended or adjusted under 35 U.S.C. 154(b) by 0 days.

(21) Appl. No.: 13/994,479

(22) PCT Filed: Dec. 8, 2011

(86) PCT No.: PCT/FR2011/052906
§ 371 (c)(1),
(2), (4) Date: Jun. 14, 2013

(87) PCT Pub. No.: WO2012/080622
PCT Pub. Date: Jun. 21, 2012

(65) Prior Publication Data
US 2013/0266522 A1    Oct. 10, 2013

(30) Foreign Application Priority Data
Dec. 14, 2010  (FR) ...................................... 10 04856

(51) Int. Cl.
*A61K 8/99*  (2006.01)
*A61Q 11/00*  (2006.01)

(52) U.S. Cl.
USPC .......................................................... 424/50

(58) Field of Classification Search
None
See application file for complete search history.

(56) References Cited

U.S. PATENT DOCUMENTS

| | | | |
|---|---|---|---|
| 7,556,654 B1 | 7/2009 | Nero | |
| 2003/0153482 A1* | 8/2003 | Mumoli | 510/446 |
| 2004/0002557 A1* | 1/2004 | Qian | 523/113 |
| 2004/0022806 A1 | 2/2004 | Wikner | |

FOREIGN PATENT DOCUMENTS

| | | |
|---|---|---|
| DE | 3416332 A1 | 11/1985 |
| DE | 102007030406 A1 | 1/2009 |
| EP | 1433388 A1 | 6/2004 |
| EP | 1977756 A1 | 10/2008 |
| WO | 2006027248 A2 | 3/2006 |

OTHER PUBLICATIONS

International Search Report for corresponding International Application No. PCT/FR2011/052906.

* cited by examiner

*Primary Examiner* — Ileana Popa
*Assistant Examiner* — Nicole Babson
(74) *Attorney, Agent, or Firm* — Egbert Law Offices, PLLC

(57) ABSTRACT

An algal extract-based composition for oro-dental use is provided. This composition comprising a mixture of algae with at least *Ascophyllum nodosum* and *Fucus* spp. is characterized in that said mixture of algae has a proportion of *Ascophyllum nodosum* of at least 90% of the weight of the mixture and that the proportion of *Fucus* spp. is at most 10% of the weight of the mixture, and in that said extract is combined with a natural surfactant and/or with a zeolite or a mixture of zeolites. Uses of said composition, in particular for dental prevention and/or care, are also provided. Applications in the oro-dental field, both preventively and curatively.

10 Claims, 2 Drawing Sheets

ALGAL EXTRACT-BASED COMPOSITION FOR ORO-DENTAL USE

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a product for oro-dental use.

More particularly, the product under the present invention acts against the formation of dental plaque and also against inflammatory conditions of the gingival and periodontal tissue. In what follows, the algal extract-based composition for oro-dental use will be described in relation to the prophylaxis of dental plaque, this being a nonlimiting and purely illustrative example.

2. Description of Related Art Including Information Disclosed Under 37 CFR 1.97 and 37 CFR 1.98

Dental plaque is an extremely clinging substance which is deposited on the teeth. It forms during the day and at night, between brushing sessions. It consists of saliva proteins, food sugars, and a very large number of bacteria and their toxins. The bacteria present metabolize the sugars and produce corrosive acids. When it is not removed by brushing the teeth, dental plaque hardens and calcifies so as to constitute tartar. Only descaling carried out by a dentist can remove it.

The accumulation of dental plaque creates an environment that is unfavorable for the gums. The bacteria forming the plaque will exert negative effects on the cells of the gums: oxidative stress, inflammatory stress. The production of free radicals and also the massive release of inflammation mediators will result in destruction of the gum connective tissue. The pathological conditions which occur are gingivitis and periodontitis. It is known that the current abrasives for preventing the occurrence of dental plaque are generally too powerful. They thus have the drawbacks of irritating the gum and damaging the tooth enamel.

Inflammatory gum conditions are common. In addition to being caused by the presence of dental plaque, they can also result from brushing the teeth too aggressively, wearing dental apparatuses, smoking, etc. It is known practice to use antibacterial agents to combat these drawbacks. These antibacterial agents are not very selective for the bacteria that they eliminate, for instance chlorhexidine: they eliminate both pathogenic and nonpathogenic bacteria. Furthermore, these antibacterial agents are not recommended for lengthy use.

Oral and dental care preparations containing algal exist, for instance document EP 1 328 285. That document presents an algae product which prevents the bacterial formation of dental plaque.

On the other hand, that document does not present the use of an algal product for the purpose of limiting oro-dental inflammation and oro-dental oxidation, and does not address tissue degeneration related to periodontitis.

Thus, generally, the current products, whether they are algae-based or based on other substances, are mainly aimed at antibacterial activity and few of them address inflammatory conditions or tissue degeneration related to periodontitis.

Another state of the art is illustrated by document FR 2 914 190 which uses an algal extract intended for the treatment of inflammatory processes. The teaching of that document shows how to obtain an algal extract which has a high phenolic compound content and its use in the pharmaceutical field intended for the treatment of inflammatory processes.

However, the teaching of that document does not present the advantage of combining an antibacterial active agent with an algal extract which has the effect of increasing the reduction in dental plaque.

Another state of the art is illustrated by document WO 2006/027248 which describes plants of the family Fucaceae which inhibit an enzyme produced by the bacteria in dental hygiene. The drawback is that these plants only act on the enzyme and not on the bacteria. Consequently, the bacteria are still present. Another drawback is that this solution acts only on the biofilm.

The purpose of the present invention is to obtain a product based on a mixture of algae which allows oro-dental hygiene prophylactic synergies.

SUMMARY OF THE INVENTION

The invention proposes a composition for oro-dental use which makes it possible in particular to limit the risks of periodontopathies, this composition containing an extract of brown algae comprising a mixture of algae with at least *Ascophyllum nodosum* and *Fucus* spp. characterized in that:
  said mixture of algae has a proportion of *Ascophyllum nodosum* of at least 90% of the weight of the mixture and a proportion of *Fucus* spp. of at most 10% of the weight of the mixture,
  the extract is combined with a natural surfactant and/or with a zeolite or a mixture of zeolites.

According to advantageous characteristics of the present invention:
  the mixture of *Ascophyllum nodosum* and *Fucus* spp. is less than or equal to 1.5%, preferably taken in the value range of between 0.1% and 1% of the weight of the composition, limits included,
  the natural surfactant is present at less than or equal to 2% of the weight of the composition, preferably from 0.1% to 1.5%, advantageously from 0.25% to 1% or even from 0.5% to 0.7%,
  the natural surfactant is a sophorose lipid,
  the zeolite or the mixture of zeolites is between 0.1% and 1% of the weight of the composition, preferably from 0.25% to 0.75%, advantageously from 0.35% to 0.65% or even 0.5%,
  the zeolite or the mixture of zeolites comprises at least one silver-loaded zeolite,
  the or at least one zeolite is a mixture of silicon oxide and aluminum oxide,
  the composition is combined with any excipient required for its galenical formation.

Furthermore, the present invention relates to a use of such a composition for:
- dental prevention and/or care,
- combating gingival inflammation,
- combating oxidative stress of gum cells, or
- combating the formation of the bacterial biofilm.

In order to carry out at least one of these uses, the algae-based composition is integrated into a toothpaste or into a mouthwash solution or into a tool for dental or oral use.

The advantages of the present invention are, inter alia, correctly maintaining the gums and the teeth by remedying the drawbacks of the prior art. The present invention proposes a solution for daily use in the prevention and treatment of the establishment of dental plaque and of periodontal inflammation.

The present invention is based on the unexpected discovery that a composition based on an extract of brown algae comprising a mixture of algae with at least *Ascophyllum nodosum* and *Fucus* spp. has considerable effects on oro-dental prevention and treatment.

The term "*Fucus* spp." is intended to mean all the subspecies of *Fucus*.

The algal extract-based composition comprises a natural surfactant and a zeolite or a mixture of zeolites which makes it possible in particular to effectively combat gingival inflammation, oxidative stress of gum cells and bacterial biofilm formation.

Unexpectedly and with a symbiosis effect, the present invention makes it possible, using the combination of an antibacterial active agent in the form of a zeolite or a mixture of zeolites with a mixture of brown algae, to effectively promote the combating of bacterial biofilm formation.

BRIEF DESCRIPTION OF THE SEVERAL VIEWS OF THE DRAWINGS

The invention will be understood more clearly from the description given hereinafter of an embodiment given by way of nonlimiting example, with reference to the following appended figures.

DETAILED DESCRIPTION OF THE INVENTION

Figure 1:
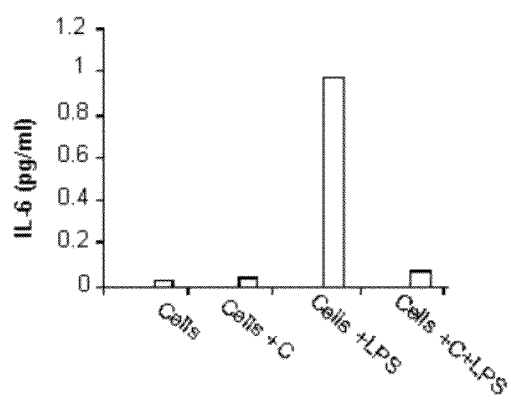
FIG. 1 is a representation of the anti-inflammatory effect using gum fibroblasts for the reduction of interleukin-6.

The subject of the present invention is the use of an algal extract-based composition intended for oro-dental hygiene use, it being possible for this use to relate to prevention, care or hygiene.

The purpose of the present invention is to prevent oro-dental problems by combating the three effects mentioned hereinafter, related in particular to dental plaque formation.

According to the present invention, the composition for oro-dental use based on an extract of brown algae comprising a mixture of algae with at least *Ascophyllum nodosum* and *Fucus* spp. is characterized in that the proportion of *Ascophyllum nodosum* is at least 90% and that the proportion of *Fucus* spp. is at most 10%, and in that said extract is combined with a natural surfactant and/or with a zeolite or a mixture of zeolites.

*Ascophyllum nodosum* and the *Fucus* species, in particular but not in a limiting manner *Fucus vesiculosus*, are types of widespread brown algae.

It is known that a surfactant modifies the surface tension between two surfaces by exhibiting two parts of different polarity, one lipophilic and apolar and the other hydrophilic and polar. There are numerous surfactants of natural origin. Mention may be made, inter alia, of surfactants based on sugar or glucosides or surfactants of acylglutamate type.

A sophorose lipid is preferred as surfactant of natural origin according to the invention. Sophorose is a naturally existing disaccharide. It consists of two glucose units linked via a glycosidic linkage. It is an isomer of maltose and of sucrose. Sophorose can be combined with lipids to give sophorose lipids or sophorolipids which have the particularity of reducing the surface tension of water.

Generally, a zeolite is a microporous mineral belonging to the silicate group, tectosilicate subgroup, in which they form a family comprising hydrated aluminosilicates of metals of groups IA and IIA of the Periodic Table of Elements, such as calcium, magnesium and potassium.

There are two types of zeolite, namely natural and synthetic. These zeolites are structurally complex crystalline inorganic polymers based on an indefinite three-dimensional succession of structures connected at four points formed of tetrahedral aluminum oxide, in particular $AlO_4$, and tetrahedral silicon oxide, in particular $SiO_4$, these structures being bonded to one another via an oxygen ion exchange. Each tetrahedral $AlO_4$ present in the structure contributes a strong negative charge which is counterbalanced by one or more cations, such as $Ca^{2+}$, $Mg^{2+}$ or $K^+$.

It is understood that the zeolite included in the composition or at least one zeolite of the mixture of zeolites allows the slow release of silver ions, having an antimicrobial effect, i.e. a family of substances which kills the bacteria or slows the growth of the microorganisms. As an alternative and/or as a supplement, it is also possible to use copper and/or zinc ions.

The ions of the zeolite or of the mixture of zeolites are activated on demand in the presence of moisture or of an activating agent. For example, the silver ions combat microorganisms in three ways: by depriving said microorganisms of food, by sterilizing them and by suffocating them.

One of the effects for combating bacterial biofilm formation is the anti-inflammatory effect, another effect is the antioxidant effect and the final effect is the antibacterial effect. This will be explained in the following three examples.

The following example 1 shows the validation of the anti-inflammatory effect.

EXAMPLE 1

Anti-inflammatory Effect

In this example, the anti-inflammatory effect is demonstrated by taking gum fibroblasts which are incubated for 2 h with the selected algal extract.

A polyphenolic extract of brown algae is obtained by means of a production process which comprises the following steps: milling of the fresh algae, aqueous extraction, solid/liquid separation, filtration to remove microparticles, elimination of alginates by precipitation, elimination of iodine, then spray drying.

This extract is an extract of brown algae which is a mixture of 90% of *Ascophyllum nodosum* and 10% of *Fucus* spp. These fibroblasts are then subjected to an inflammatory stress using the *Escherichia coli* lipopolysaccharide biological agent for 24 h. The results of the various inflammation mediators are assayed and are shown in FIGS. 1 and 2.

In these two figures, the algal extract is denoted C, the cells correspond to gum fibroblasts and a lipopolysaccharide biological agent of the *Escherichia coli* strain is denoted by LPS.

Figure 2:
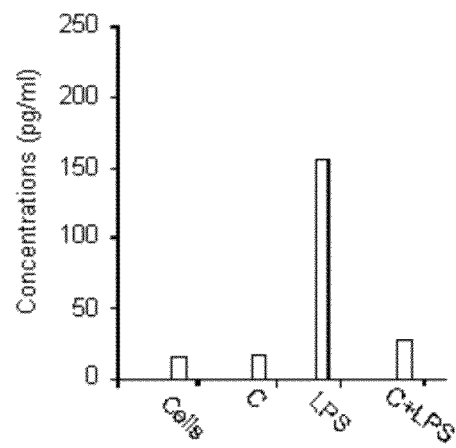
FIG. 2 is a representation of the anti-inflammatory effect using gum fibroblasts for the reduction of tumor necrosis factor-α.

FIG. 1 is a representation of the anti-inflammatory effect, using gum fibroblasts for the reduction of interleukin-6. "Interleukin-6" is understood to be a key cytokine in the regulation of acute and chronic inflammation. It is known that hyperproduction of interleukin-6 can cause an inflammation.

FIG. 1 makes it possible to appreciate first of all that the extract C does not induce any inflammatory stress since the gum fibroblasts do not react with the algal extract. Next, it makes it possible to see that the anti-inflammatory effect of the extract C is verified. This is because, by comparing it with a first mixture of cells and of LPS with a second mixture of cells, of LPS and of the algal extract, it is observed that the algal extract limits the impact of the LPS. Consequently, the results indicate that the algal extract makes it possible to reduce interleukin-6 production.

FIG. 2 is a representation of the anti-inflammatory effect using gum fibroblasts for the reduction of tumor necrosis factor-α production. "Tumor necrosis factor-α" is understood to be a factor which reveals a sign of inflammation through the measurement of its concentration. Indeed, a local increase in the concentration of tumor necrosis factor-α is an indication of the cardinal signs of inflammation such as redness, heat, tumefaction, pain, etc.

In the same way as FIG. 1, FIG. 2 shows that the extract C does not induce any inflammatory stress since the gum fibroblasts do not react with the algal extract. It confirms that the anti-inflammatory effect of the extract C is verified; by comparing a first mixture comprising cells and LPS with a second mixture comprising cells, LPS and the algal extract, it is observed that the algal extract limits the impact of the LPS. Consequently, the results indicate that the algal extract makes it possible to reduce tumor necrosis factor-α production.

In order to characterize the dose of algal extract responsible for the anti-inflammatory effect, an experimental protocol was carried out on macrophages, which are major cells of the inflammatory response.

Figure 3:
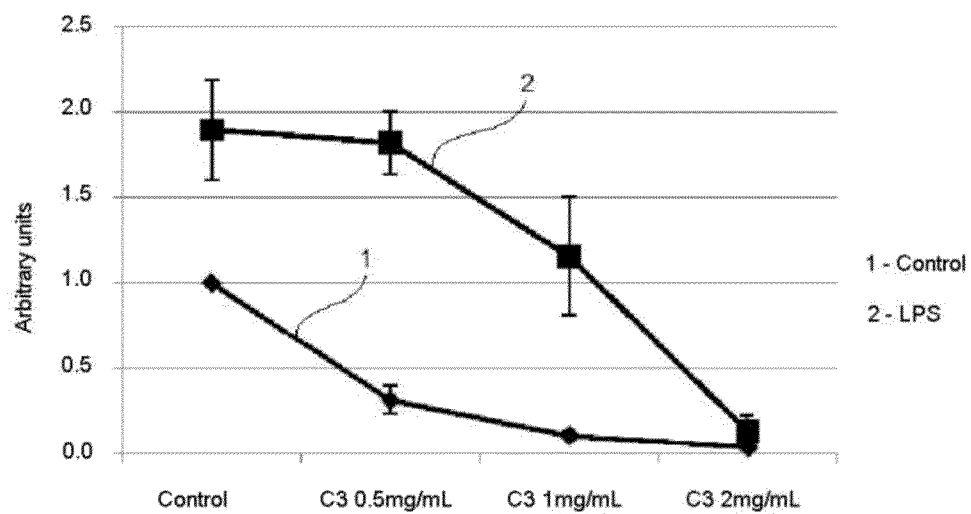
FIG. 3 is a representation of the anti-inflammatory effect on macrophages for the inhibition of interleukin-6 production.
Figure 4:
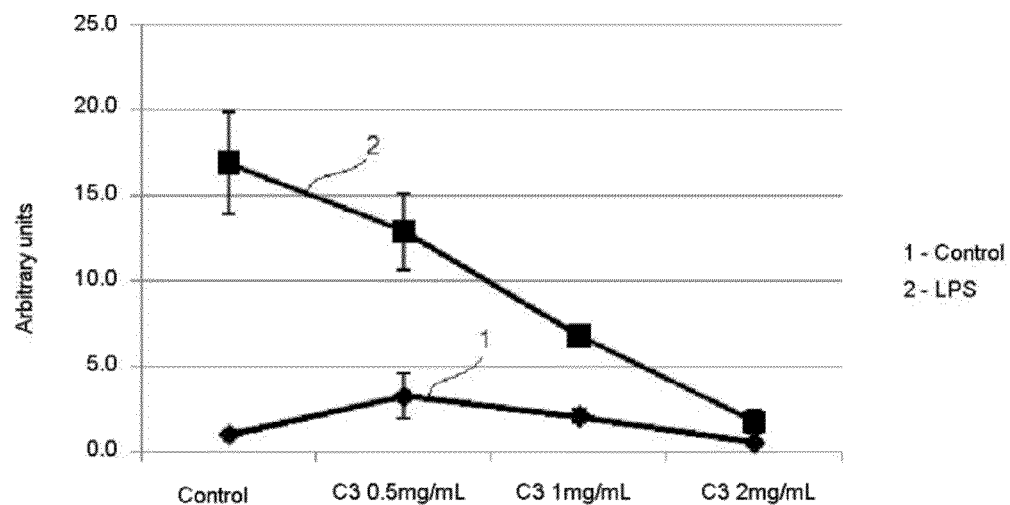
FIG. 4 is a representation of the anti-inflammatory effect on macrophages for the inhibition of tumor necrosis factor-α production.

In FIGS. 3 and 4, the algal extract is denoted C3 and corresponds to a mixture of extract of *Ascophyllum nodosum* and *Fucus* spp. algae. These figures represent the result Of the experimental protocol. Thus, macrophages were incubated in a first step with various concentrations of the algal extract for 2 hours before being stimulated via an inflammatory stress with LPS at 0.5 µg/ml for 24 hours. The proinflammatory cytokines interleukin-6 and tumor necrosis factor-α are assayed in the cell supernatant using a biochemical technique of the ELISA type (enzyme-linked immunosorbent assay).

The results of FIG. 3 show that the algal extract inhibits the inflammation induced by the production of interleukin-6 by the macrophages stimulated with the lipopolysaccharide biological agent, in a dose-dependent manner. Indeed, the more the amount of C3 increases, the more the interleukin-6 production decreases, which clearly shows the dependence in relation to the dose administered.

In the same way, FIG. 4 shows the same result concerning the production of tumor necrosis factor-α.

These two figures clearly show that the algal extract is an effective inflammation-limiting agent.

The following example 2 shows the validation of the antioxidant effect.

EXAMPLE 2

Antioxidant Effect

Owing to its chemical structure, the algal extract has an intrinsic antioxidant potential.

A first series of assays was carried out in vitro, on acellular models:
 evaluation of the measurement of the antioxidant capacities in biological samples: the marine extract has an activity of 296 µmol Eq Trolox/g;
 evaluation of the superoxide anion-scavenging capacity: the algal extract at 0.1% has an activity of 87 SOD/min;
 evaluation of the hydroxyl radical-scavenging capacity: the algal extract at 1% has an activity of 1556 Eq benzoic acid (mg/l).

These three series of assays indicate that the algal extract has the capacity to inhibit the formation of free radicals, i.e. which have an antioxidant capacity, but also to scavenge reactive oxygen species, i.e. a superoxide anion and a hydroxyl radical. The algal extract therefore acts by preventing an oxidative stress, but also by repairing the oxidative compounds already present.

In order to confirm that these results are physiologically real, the antioxidant effects of this extract on the cellular scale were studied. Firstly, cells of the gingival epithelium were incubated for 1 hour with the algal extract at 0.1%, denoted active agent C in FIG. 5. Next, the oxidative stress is stimulated with the lipopolysaccharide biological agent, denoted LPS in FIG. 5, of the *Porphyromonas gingivalis* strain at 10 µg/ml for 2 hours. Isoprostanes are formed via a nonenzymatic radical process of peroxidation of polyunsaturated fatty acids, i.e. membrane-phospholipid arachidonic acids. The measurement of the production of isoprostanes in the cell supernatant is carried out by LCMS, i.e. liquid chromatography/mass spectrometry.

Figure 5:
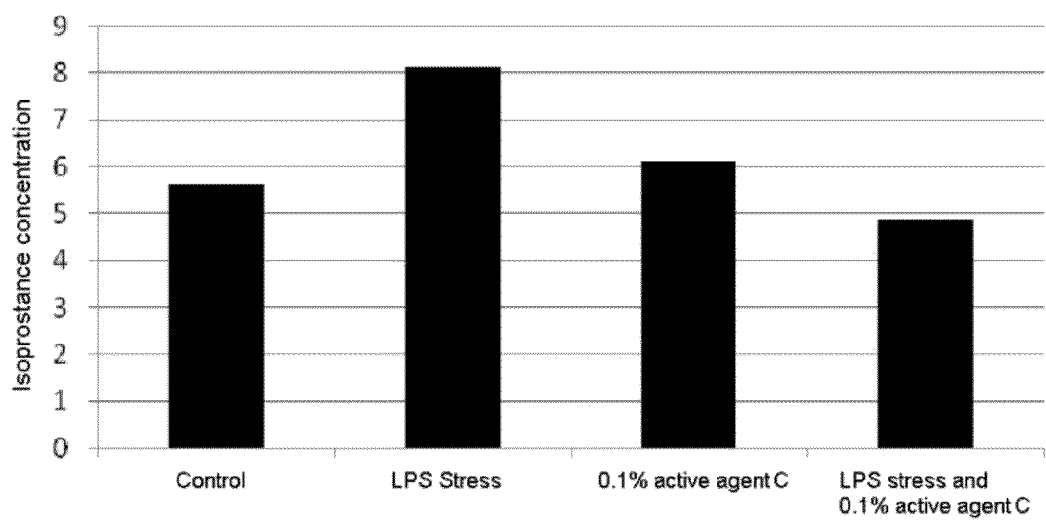
FIG. 5 is a representation of the antioxidant effect on epithelium cells.

FIG. 5 shows the results of the antioxidant effect. Indeed, the results of FIG. 5 show that the algal extract inhibits the oxidative stress induced on the gingival cells by the lipopolysaccharide biological agent. It can be appreciated that the amount of isoprostanes in pg/ml induced by the mixture of LPS and active agent C is smaller than the amount of isoprostanes induced by the LPS stress.

Furthermore, the algal extract is applied before the oxidative stress so as to prevent the damage induced by the oxidative stress. The data of FIG. 5 clearly show that the mixture of the stress by the lipopolysaccharide biological agent and of the algal extract denoted C acts by reducing the damage caused by an oxidative stress. Indeed, it can be appreciated that the amount of isoprostanes in pg/ml induced by the mixture of LPS and active agent C is smaller than the amount of isoprostanes induced by the active agent C.

The following example 3 shows the validation of the antibacterial effect.

EXAMPLE 3

Antibacterial Effect

The antibacterial effects are tested on the strains of oral flora involved in periodontitis. Preferentially, a *Porphyromonas gingivalis* and also a commensal bacterium, for example *Streptococcus gordonii*, i.e. bacteria which live on waste found outside the tissues, were chosen. The present invention thus shows its value through the combination of the algal extract with other ingredients known for their antibacterial role in order to prevent the bacterial biofilm formation.

Below is a table which represents the combination of a silver zeolite and the algal extract:

|  |  | Silver zeolite | Algal extract | Silver zeolite + algal extract |
|---|---|---|---|---|
| Antibacterial activity expressed in colony-forming units/ml | P. gingivalis | ↓1.60 × $10^7$ ± 0.05 | No effect | ↓2.46 × $10^7$ ± 0.16 |
|  | S. gordonii | No effect | No effect | No effect |
| Anti-biofilm activity (preventive effect) expressed in % infection | P. gingivalis | 88.81 ± 0.22 | No effect | <0 |
|  | S. gordonii | 49.66 ± 0.34 | No effect | <0 |
|  | P. gingivalis + S. gordonii | 93.66 ± 0.13 | No effect | 73.26 ± 2.09 |

The analysis of this table makes it possible to reveal that the mixture of 0.5% of zeolite and 0.5% of algal extract has the advantage of not being accompanied by effects on the commensal flora of the mouth. Indeed, as the results of the table indicate, there is no effect with *Streptococcus gordonii* which simulates a complex set of bacteria and protozoa, this flora being essential to good oro-dental bacterial equilibrium.

Furthermore, the mixture of 0.5% of zeolite and 0.5% of algal extract shows an unexpected increase in the antibacterial effect.

In a manner other than that with zeolite, the combination with a surfactant which has an anti-biofilm effect on *Porphyromonas gingivalis* and *Streptococcus gordonii* can be used.

Consequently, the combination of 0.5% of zeolite or of a mixture of zeolites, in particular comprising silver, of 0.5% of an algal extract-based marine active agent and of a surfactant makes it possible to obtain a product with a strong antibacterial power and a powerful anti-biofilm effect. These two elements are important for good oro-dental hygiene.

Thus, the composition according to the present invention can have several uses which are nonlimiting:
  use for dental prevention and/or care,
  use for combating gingival inflammation,
  use for combating oxidative stress of gum cells,
  use for combating bacterial biofilm formation.

The composition can also be combined with any excipient required for its galenical formation, such as a gelling agent, a flavoring, an abrasive agent, a dye, an opacifier, etc.

In order to allow these uses, the composition may be integrated into a toothpaste, into a mouthwash solution or into a tool for treating the teeth or the mouth. As examples of tools, mention may be made in a nonlimiting way of a toothbrush or dental floss, in which case the composition is integrated into the hairs of the brush or onto the thread of the dental floss, for example as a coating thereof.

The invention claimed is:

1. A composition for oro-dental use comprising:
   an algae mixture comprising at least *Ascophyllum nodosum* and *Fucus* spp. in which the proportion of *Ascophyllum nodosum* is at least 90% of a total weight of the mixture and the proportion of *Fucus* ssp. is at most 10% of the total weight of the mixture; and
   at least one silver-loaded zeolite,
   wherein the mixture of *Ascophyllum nodosum* and *Fucus* spp. is less than or equal to 1.5% of a total weight of the composition.

2. The composition of claim 1, further comprising:
   a natural surfactant of less than or equal to 2% of the total weight of the composition.

3. The composition of claim 2, said natural surfactant being a sophorose lipid.

4. The composition of claim 1, the silver-loaded zeolite being between 0.1% and 1% of the total weight of the composition.

5. The composition of claim 1, the silver-loaded zeolite having a mixture of silicon oxide and aluminum oxide.

6. The composition of claim 1, further comprising:
   a galenical excipient in an amount suitable for galenical formation.

7. The composition of claim 1, wherein the composition is used for treatment of inflammatory gingival and periodontal tissue.

8. The composition of claim 1, wherein the composition is used as a antibacterial agent.

9. The composition of claim 1, wherein the composition is used as an anti-inflammatory agent.

10. A toothpaste of mouthwash solution for dental or oral use comprising the composition of claim 1.

* * * * *